(12) United States Patent
Hsiung et al.

(10) Patent No.: US 11,413,419 B2
(45) Date of Patent: Aug. 16, 2022

(54) NASAL CANNULA HAVING SLIDING TRACK MECHANISM

(71) Applicant: Besmed Health Business Corp., New Taipei (TW)

(72) Inventors: Tao-Tsun Hsiung, New Taipei (TW); Xu-Xiang Wang, New Taipei (TW)

(73) Assignee: BESMED HEALTH BUSINESS CORP., New Taipei (TW)

( * ) Notice: Subject to any disclaimer, the term of this patent is extended or adjusted under 35 U.S.C. 154(b) by 561 days.

(21) Appl. No.: 16/366,091

(22) Filed: Mar. 27, 2019

(65) Prior Publication Data

US 2019/0298961 A1 Oct. 3, 2019

(30) Foreign Application Priority Data

Apr. 3, 2018 (TW) .................................. 107112202

(51) Int. Cl.
*A61M 16/06* (2006.01)
*A61M 16/08* (2006.01)
*A61L 29/06* (2006.01)
*A61L 29/14* (2006.01)

(52) U.S. Cl.
CPC ......... *A61M 16/0816* (2013.01); *A61L 29/06* (2013.01); *A61L 29/14* (2013.01); *A61M 16/0666* (2013.01); *A61M 16/0683* (2013.01); *A61M 2205/0216* (2013.01)

(58) Field of Classification Search
CPC ........ A61L 29/042; A61L 29/06; A61L 29/14; A61M 16/0003; A61M 16/0057; A61M 16/0066; A61M 16/0069; A61M 16/024; A61M 16/04; A61M 16/0415; A61M 16/0622; A61M 16/0666; A61M 16/0672; A61M 16/0677; A61M 16/0683; A61M 16/0688; A61M 16/08; A61M 16/0816; A61M 16/0858; A61M 16/0875; A61M 16/109; A61M 16/1095; A61M 16/122; A61M 16/16; A61M 16/161; A61M 2016/003; A61M 2202/0208; A61M 2205/0216; A61M 2205/33; A61M 2205/3334; A61M 2205/3368;
(Continued)

(56) References Cited

U.S. PATENT DOCUMENTS

| | | | | |
|---|---|---|---|---|
| 10,478,580 | B2 * | 11/2019 | Klenner | A61M 16/0858 |
| 2004/0261797 | A1 * | 12/2004 | White | A61M 16/0066 128/206.11 |

(Continued)

*Primary Examiner* — Annette Dixon
(74) *Attorney, Agent, or Firm* — Bacon & Thomas, PLLC

(57) ABSTRACT

A nasal cannula having sliding track mechanism, the nasal cannula has a flexible nasal prong body, the nasal prong body is combined with a rigid sliding track frame, an elastic portion of the nasal prong body is formed on the sliding track frame, an outside of the elastic portion is provided with a pair of nasal prongs; wherein two sides of the sliding track frame respectively have a track, a intake tube can be quickly combined to the nasal prong body in a sliding manner along a rigid track direction of the sliding track frame, and a gas tightness can be achieved between the nasal prong body and the intake tube, the intake tube can be quickly separated from the nasal prong body in a sliding manner along a track direction of the sliding track frame.

10 Claims, 7 Drawing Sheets

(58) Field of Classification Search
CPC .......... A61M 2205/50; A61M 2205/52; A61M 2207/00; C08L 83/04; F16L 37/248
See application file for complete search history.

(56) References Cited

U.S. PATENT DOCUMENTS

2009/0320851 A1* 12/2009 Selvarajan ........ A61M 16/0683
128/207.13
2010/0192957 A1* 8/2010 Hobson ............. A61M 16/0069
128/207.18

\* cited by examiner

NASAL CANNULA HAVING SLIDING TRACK MECHANISM

BACKGROUND OF THE INVENTION

1. Field of the Invention

The present invention relates to a nasal cannula assembly and more particularly to a nasal cannula having sliding track mechanism, a flexible nasal prong body of the nasal cannula and a rigid intake tube can be easily combined or separated by the sliding track mechanism, an elastic portion can be formed on the flexible nasal prong body, a gas tightness between the nasal prong body and the intake tube can be achieved by the elastic portion.

2. Description of Related Art

A prior-art is disclosed in U.S. Pat. No. 8,267,092, the prior-art disclosed a single flow entry nasal cannula assembly (30) which adapted for fluid intake from the left or right side, and therefore the nasal cannula assembly (30) can be configured to use in a left or right hand direction. The nasal cannula assembly (30) includes a face mount portion (32) and a gas flow manifold (35), the face mount portion (32) includes a generally tubular member defining an open tubular recess (38), at least one nasal prong (33) extending from the generally tubular member, a passage of the nasal prong (33) is fluid communicated to the open tubular recess (38) which defined by the generally tubular member; the gas flow manifold (35) can be inserted into the open tubular recess (38), the gas flow manifold (35) includes a first end and a second end. The first end of the gas flow manifold (35) can enclose at least one end of the open tubular recess (38) when the gas flow manifold (35) is inserted into the open tubular recess (38), the second end of the gas flow manifold (35) can be connected to a tubing (3); the gas flow manifold (35) includes a wall portion which connected the first end of the gas flow manifold (35) to the second end of the gas flow manifold (35), and an opening (37) defined between the first end and the second end; whereby a gas flow from the second end of the gas flow manifold (35) can pass through the opening (37), and the gas flow can enter the passage of at least one nasal prong (33).

The face mount portion of the prior art formed a tubular structure, and when the nasal cannula assembly needs to be cleaned and disinfected, a user can not easily separate the gas flow manifold from the open tubular recess. Thus, the prior-art still requires improvement.

SUMMARY OF THE INVENTION

It is therefore an object of the invention to provide a nasal cannula having sliding track mechanism, the nasal cannula comprises a rigid sliding track frame, two sides of the sliding track frame respectively have a track, a through hole formed on the sliding track frame; a flexible nasal prong body, the nasal prong body is combined with the sliding track frame, an elastic portion of the nasal prong body is formed on the sliding track frame, an outside of the elastic portion is provided with a pair of nasal prongs, an inside of the elastic portion is provided with a sealing surface, and the sealing surface is located at the through hole of the sliding track frame; a rigid intake tube, one side of the intake tube has a flow guiding portion, and the flow guiding portion has a pair of first convex portions; wherein each of the first convex portions can be inserted into each of the tracks, each of nasal prongs can be fluid communicated to an opening of the flow guiding portion, a flange of the opening can be pressed against the sealing surface, therefore a gas tightness can be achieved between the flow guiding portion and the elastic portion.

First advantages of the invention is, the intake tube can be quickly combined to the nasal prong body in a sliding manner along a track direction of the sliding track frame, and the intake tube can be quickly separated from the nasal prong body in a sliding manner along a track direction of the sliding track frame.

Second advantages of the invention is, the sliding track frame further has a pair of guiding portions, the flow guiding portion further has a pair of guiding surfaces; each of the guiding portions can slide on each of the guiding surfaces when the sliding track frame is combined with the guiding portion, and thereby guiding each of the first convex portions to insert into each of the tracks.

Third advantages of the invention is, a breathing tube can be connected with the intake tube, two tracks of the sliding track frame can limit the moving direction of the first convex portions of the flow guiding portion, therefore the first convex portions of the flow guiding portion can synchronously slide along the track direction of the sliding track frame, the flow guiding portion will be not easily offset. Moreover, the flow guiding portion is not easily separated from the tracks of the sliding track frame when the breathing tube is inadvertently pulled.

The above and other objects, features and advantages of the invention will become apparent from the following detailed description taken with the accompanying drawings.

DETAILED DESCRIPTION OF THE INVENTION

Figure 1:
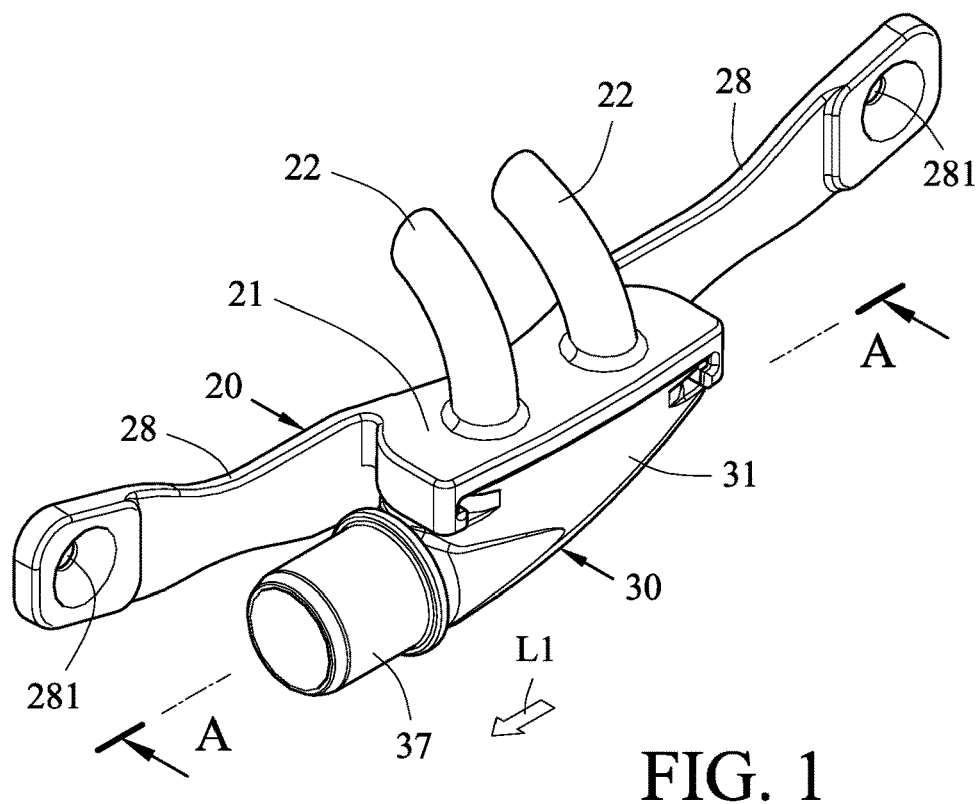
FIG. 1 is a perspective view showing a first preferred embodiment of the invention in a first combining direction.

Referring to FIGS. 1 to 11, a nasal cannula in accordance with a first preferred embodiment of the invention comprises a rigid sliding track frame 10, two sides of the sliding track frame 10 respectively have a first positioning portion 11 and a track 12, a through hole 13 is formed on the sliding track frame 10; a flexible nasal prong body 20, the nasal prong body 20 is combined with the sliding track frame 10, an elastic portion 21 of the nasal prong body 20 is formed on the sliding track frame 10, an outside of the elastic portion 21 is provided with a pair of nasal prongs 22, an inside of the elastic portion 21 is provided with a sealing surface 25, and the sealing surface 25 is located at the through hole 13 of the sliding track frame 10; a rigid intake tube 30, one side of the intake tube 30 has a flow guiding portion 31, and the flow guiding portion 31 has a pair of first convex portions 32 and a second positioning portion 33; wherein each of the first convex portions 32 can be inserted into each of the tracks 12, each of the first positioning portions 11 and each of the second positioning portions 33 can be positioned to each other, thereby limiting a relative position of the sliding track frame 10 and the flow guiding portion 31, each of nasal prongs 22 can be fluid communicated to an opening 34 of the flow guiding portion 31, a flange 35 of the opening 34 can be pressed against the sealing surface 25, therefore a gas tightness can be achieved between the flow guiding portion 31 and the elastic portion 21, the intake tube 30 can be quickly combined to the nasal prong body 20 in a sliding manner along a track direction S1 of the sliding track frame 10; each of the first convex portions 32 can be escaped from each of the tracks 12 when each of the first positioning portions 11 is separated from each of the second positioning portions 33, the intake tube 30 can be quickly separated from the nasal prong body 20 in a sliding manner along a track direction S1 of the sliding track frame 10.

Examples of the shape of the first convex portions 32, the first positioning portions 11 and the second positioning portions 33 will be illustrated below, each of the first convex portions 32 can be formed a shape of curved surface, each of the first convex portions 32 can be easily inserted into each of the tracks 12 when the sliding track frame 10 is combined with the flow guiding portion 31; the first positioning portions 11 and the second positioning portions 33 can be formed a shape of curved surface, each of the first positioning portions 11 is easily positioned in each of the second positioning portions 33 when the sliding track frame 10 is combined with the flow guiding portion 31; each of the first positioning portions 11 is easily separated from each of the second positioning portions 33 when the sliding track frame 10 is separated from the flow guiding portion 31.

Examples of the material of the sliding track frame 10, the nasal prong body 20 and the intake tube 30 will be illustrated below, the material of the nasal prong body 20 is, for example but not limited to Silicone, Thermo-Plastic-Rubber (TPR), Thermoplastic Elastomer (TPE), Thermoplastic Urethane (TPU); the material of the sliding track frame 10 and the intake tube 30 is, for example but not limited to plastic.

Examples of the further function of the sliding track frame 10 and the flow guiding portion 31 will be illustrated below, the sliding track frame 10 further has a pair of the guiding portions 16, the flow guiding portion 31 further has a pair of guiding surfaces 36; each of the guiding portions 16 can slide on each of the guiding surfaces 36 when the sliding track frame 10 is combined with the guiding portion 31, and thereby guiding each of the first convex portions 32 to insert into each of the tracks 12.

Examples of the combination manner of the nasal prong body 20 and the sliding track frame 10 will be illustrated below, the nasal prong body 20 is combined to the sliding track frame 10 by means of injection molding or bonding, the nasal prong body 20 has a stopping portion 24, the stopping portion 24 can be pressed against a first rib portion 14 of the sliding track frame 10, a second rib portion 15 of the sliding track frame 10 can be fixed to a groove 251 of the nasal prong body 20, the groove 251 is adjacent to the elastic portion 21, the nasal prong body 20 has a pair of lateral walls 26, each of the guiding portions 16 can be fixed between the lateral walls 26 and the elastic portion 21.

Examples of the further function of the flow guiding portion 31 will be illustrated below, the flow guiding portion 31 has a pair of upright wall surfaces 311, each of the upright wall surfaces 311 is located between each of the first convex portions 32 and each of the guiding surfaces 36, each of the second positioning portions 33 is disposed on each of the upright wall surfaces 311; When the sliding track frame 10 is combined with the guiding portion 31, each of the second positioning portions 33 can slide on an inside wall surface 161 of each guiding portion 16 until each of the second positioning portions 33 is positioned with each of the first positioning portions 11.

Figure 2:
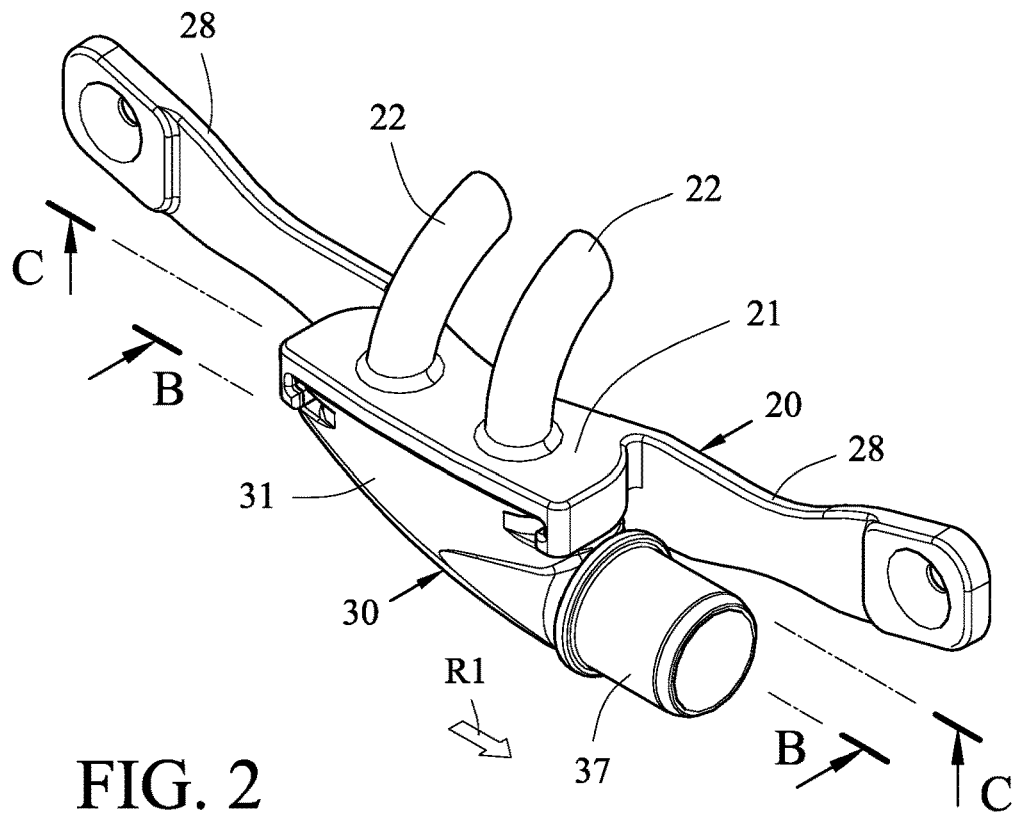
FIG. 2 is a perspective view showing a first preferred embodiment of the invention in a second combining direction.
Figure 3:
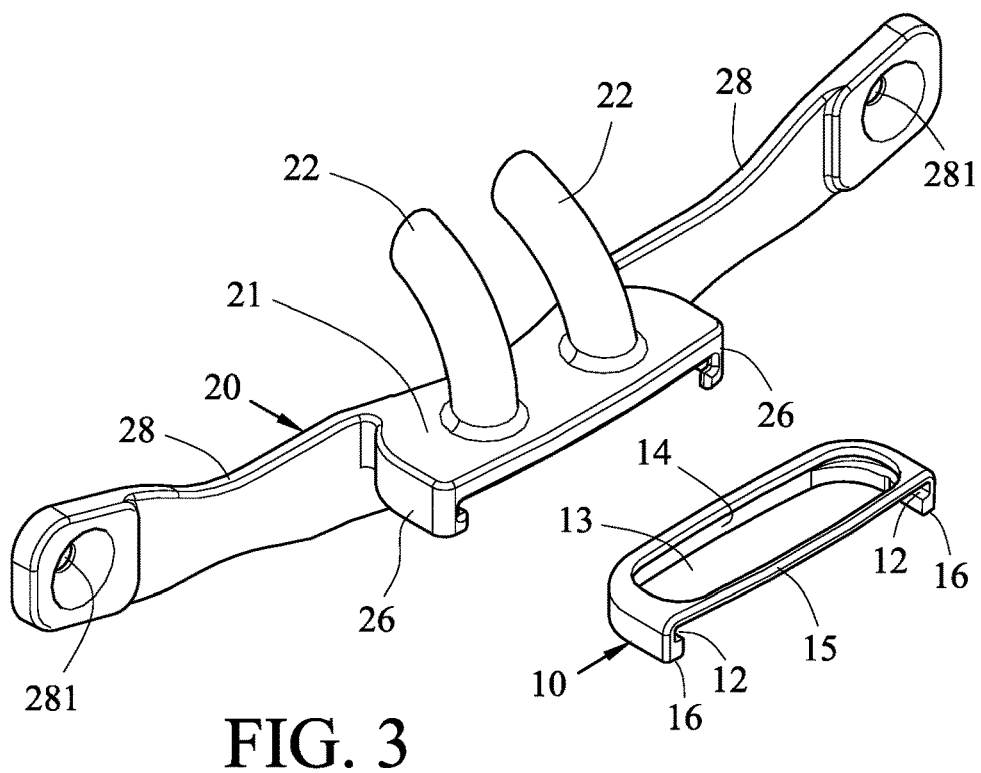
FIGS. 3 to 5 are the exploded view showing the sliding track frame and the nasal prong body.
Figure 4:
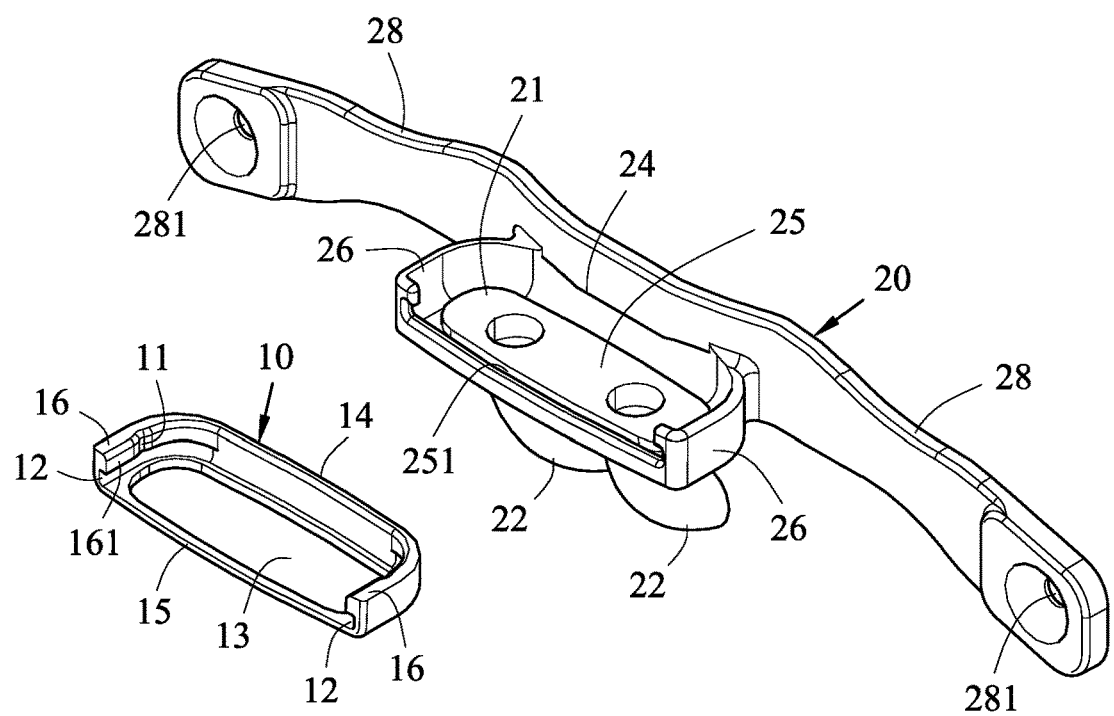
Figure 5:
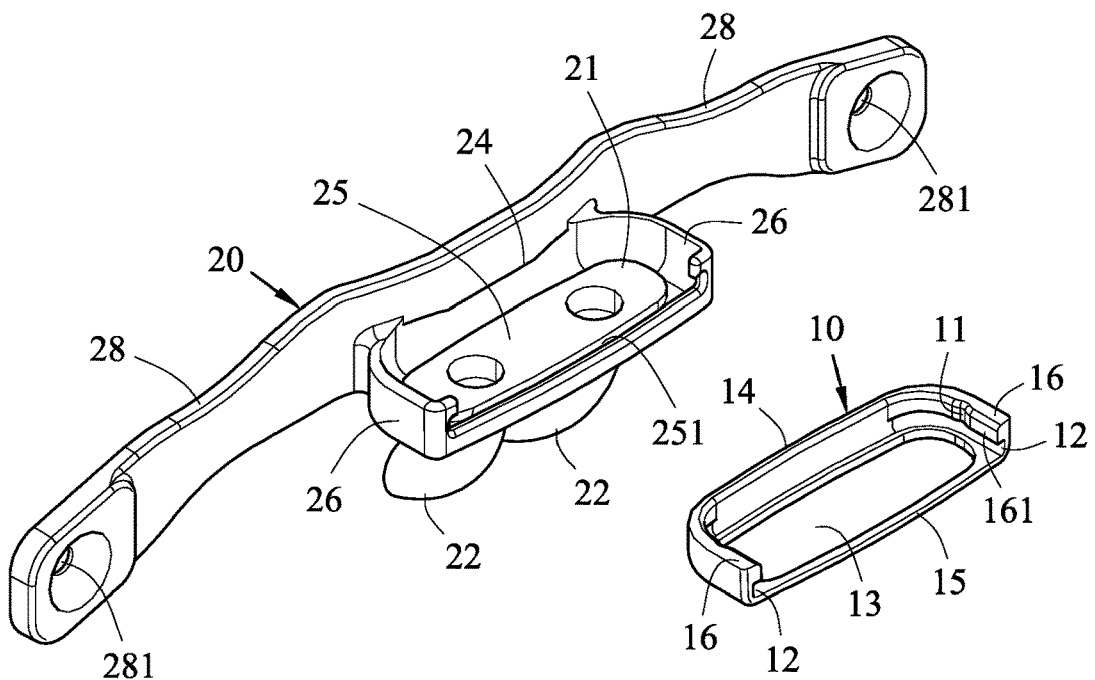
Figure 6:
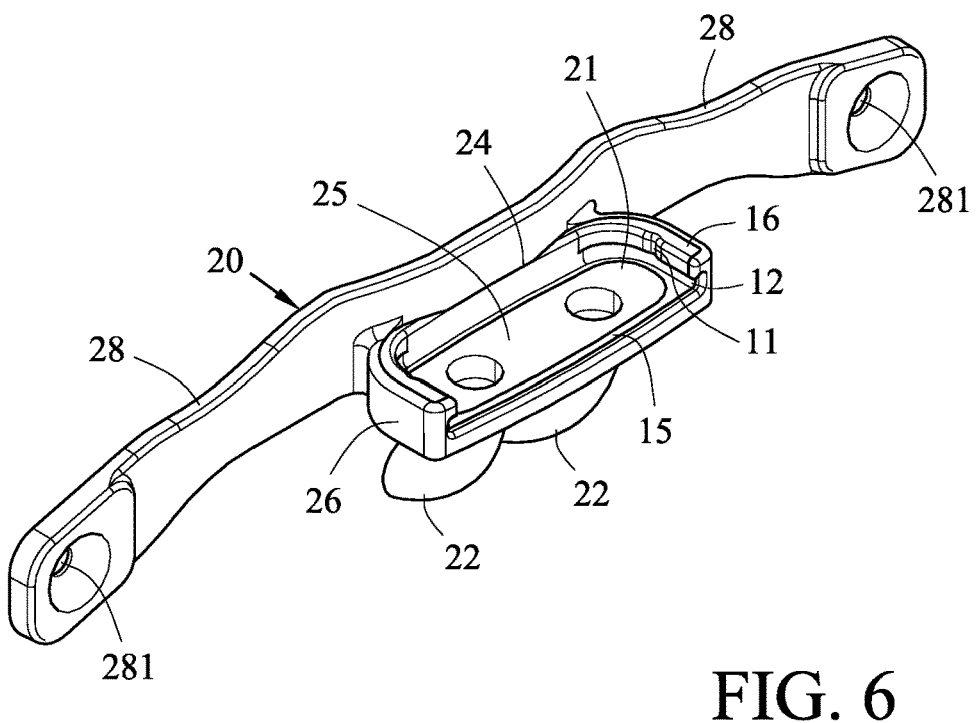
FIG. 6 is a perspective view showing a combination status of the sliding track frame and the nasal prong body.
Figure 7:
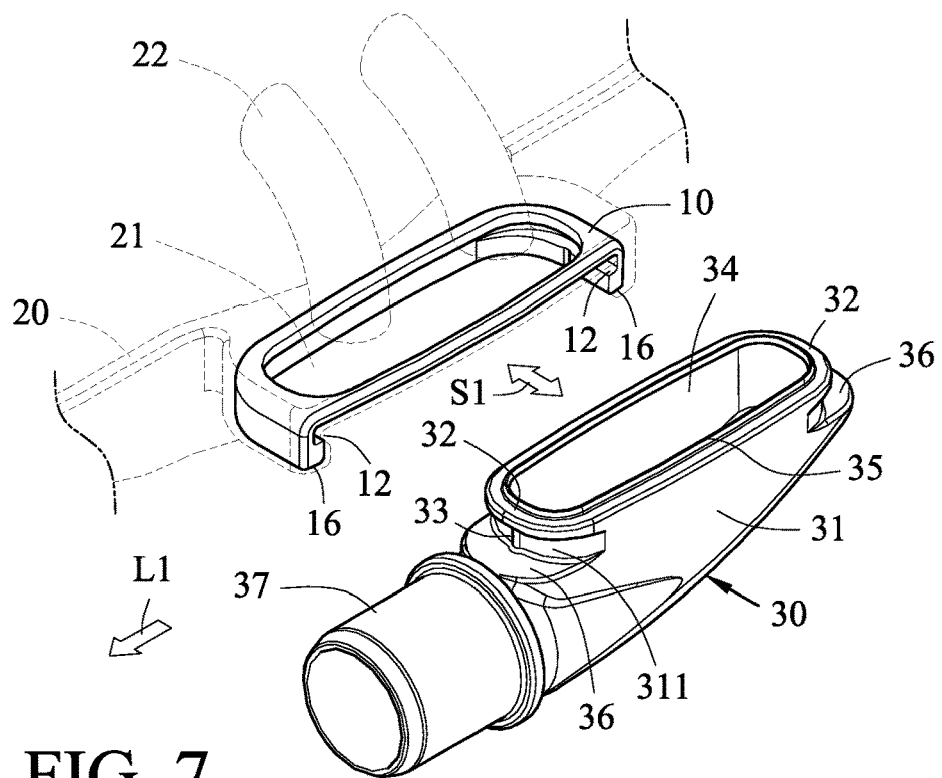
FIG. 7 is a perspective view showing a first combining direction of the sliding track frame and the intake tube.
Figure 8:
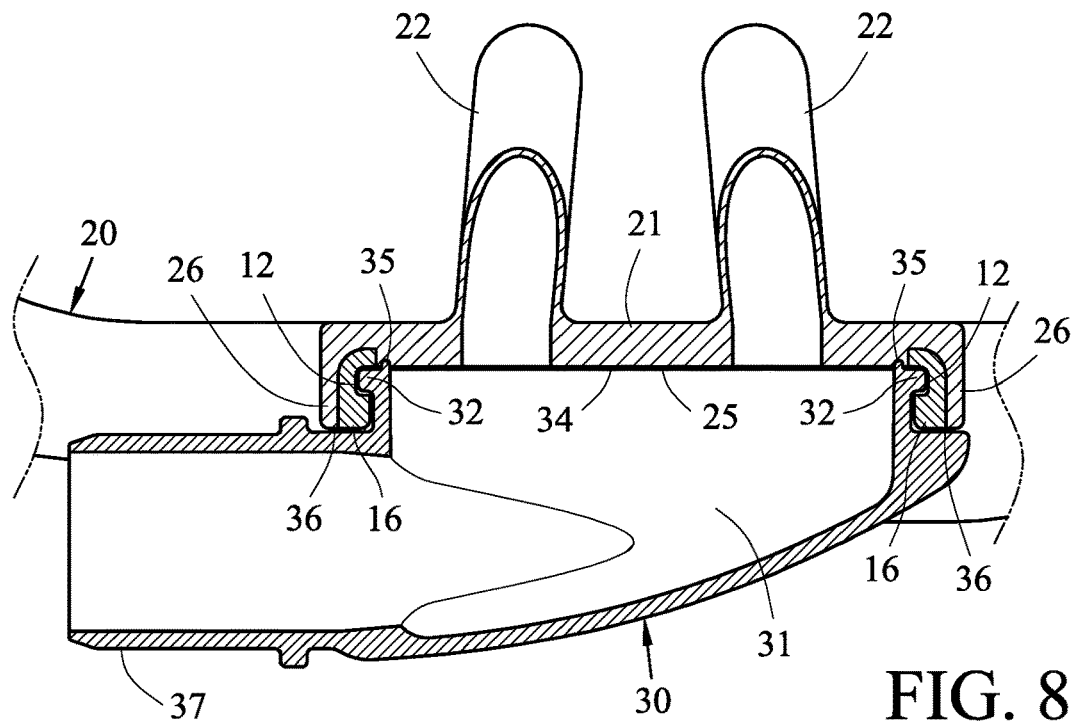
FIG. 8 is a cross-sectional view along a line A-A of FIG. 1.
Figure 9:
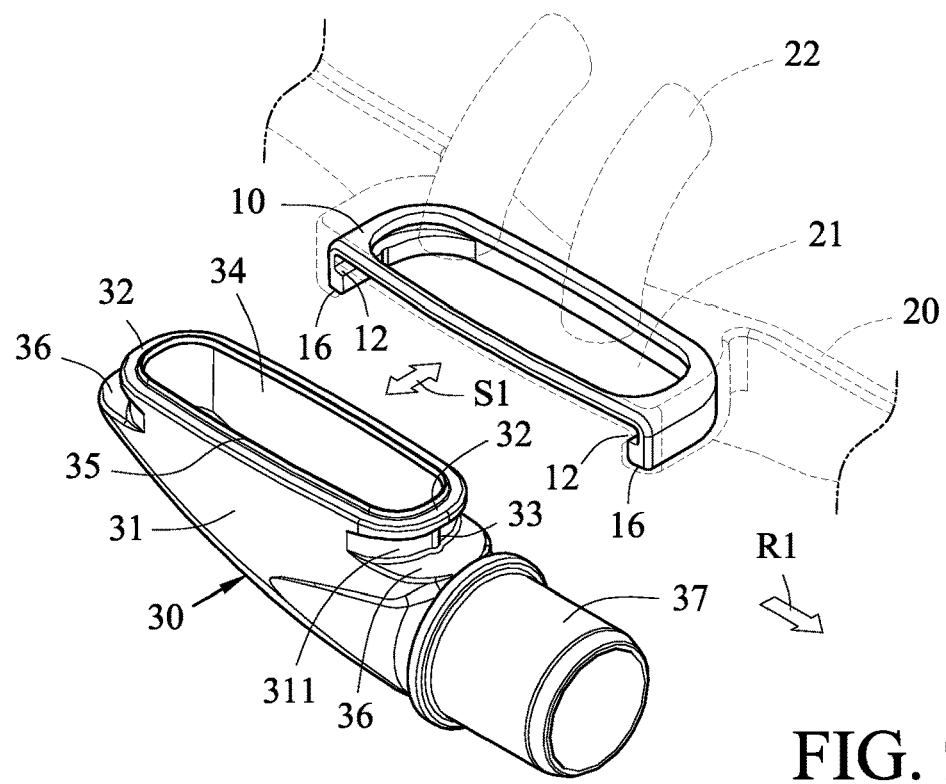
FIG. 9 is a perspective view showing a second combining direction of the sliding track frame and the intake tube.
Figure 10:
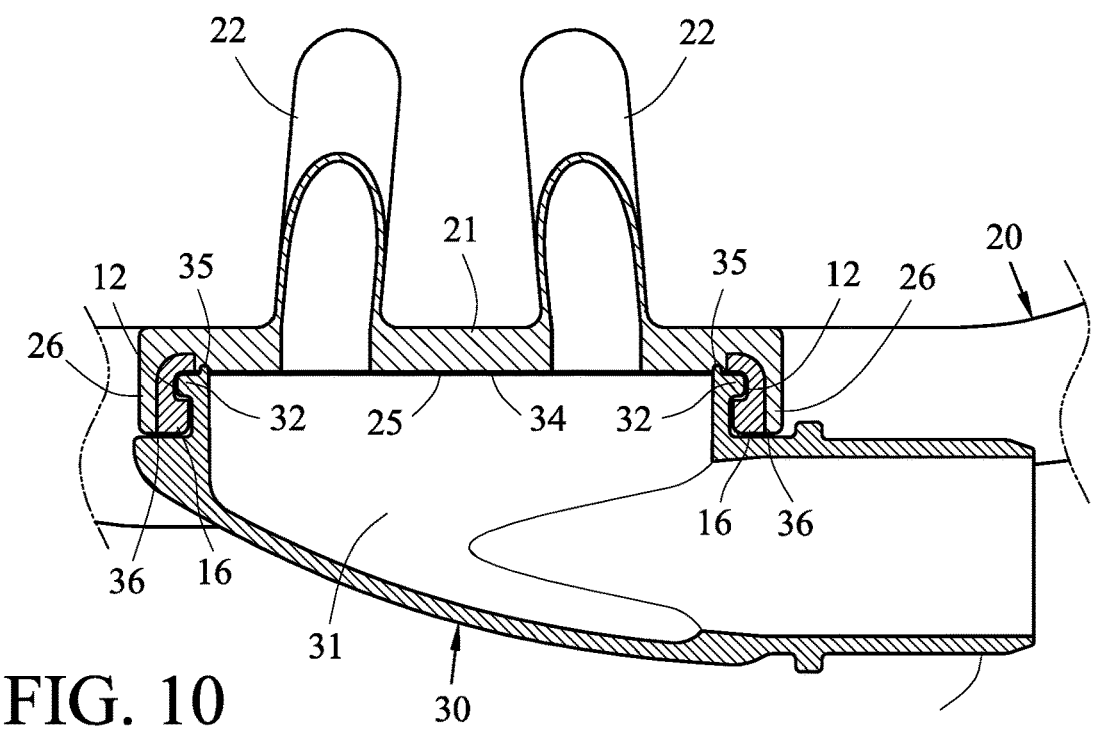
FIG. 10 is a cross-sectional view along a line B-B of FIG. 2.
Figure 11:
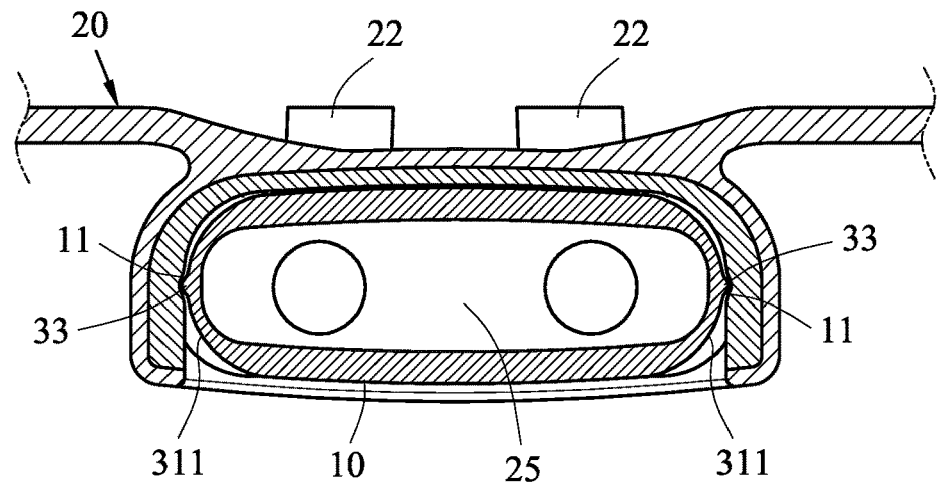
FIG. 11 is a cross-sectional view along a line C-C of FIG. 2.

Examples of the combination direction of the intake tube 30 and the sliding track frame 10 will be illustrated below, the tracks 12 are symmetrically disposed on the sliding track frame 10, the first convex portions 32 are symmetrically disposed on the flow guiding portion 31, therefore the combination direction of the intake tube 30 and the sliding track frame 10 can be quickly changed (as shown in FIGS. 7 to 10); furthermore, the first positioning portions 11 are symmetrically disposed on the sliding track frame 10, the second positioning portions 33 are symmetrically disposed on the flow guiding portion 31, therefore the combination direction of the intake tube 30 and the sliding track frame 10 can be quickly changed (as shown in FIGS. 7 to 10); When the intake tube 30 is combined to the sliding track frame 10 in a first combination direction, a connecting portion 37 of the intake tube 30 can be located in a left direction L1 of the nasal prong body 20 (as shown in FIGS. 1, 7 and 8); When the intake tube 30 is combined to the sliding track frame 10 in a second combination direction, the connecting portion 37 of the intake tube 30 can be located in a right direction R1 of the nasal prong body 20 (as shown in FIGS. 2, 9 and 10).

Figure 12:
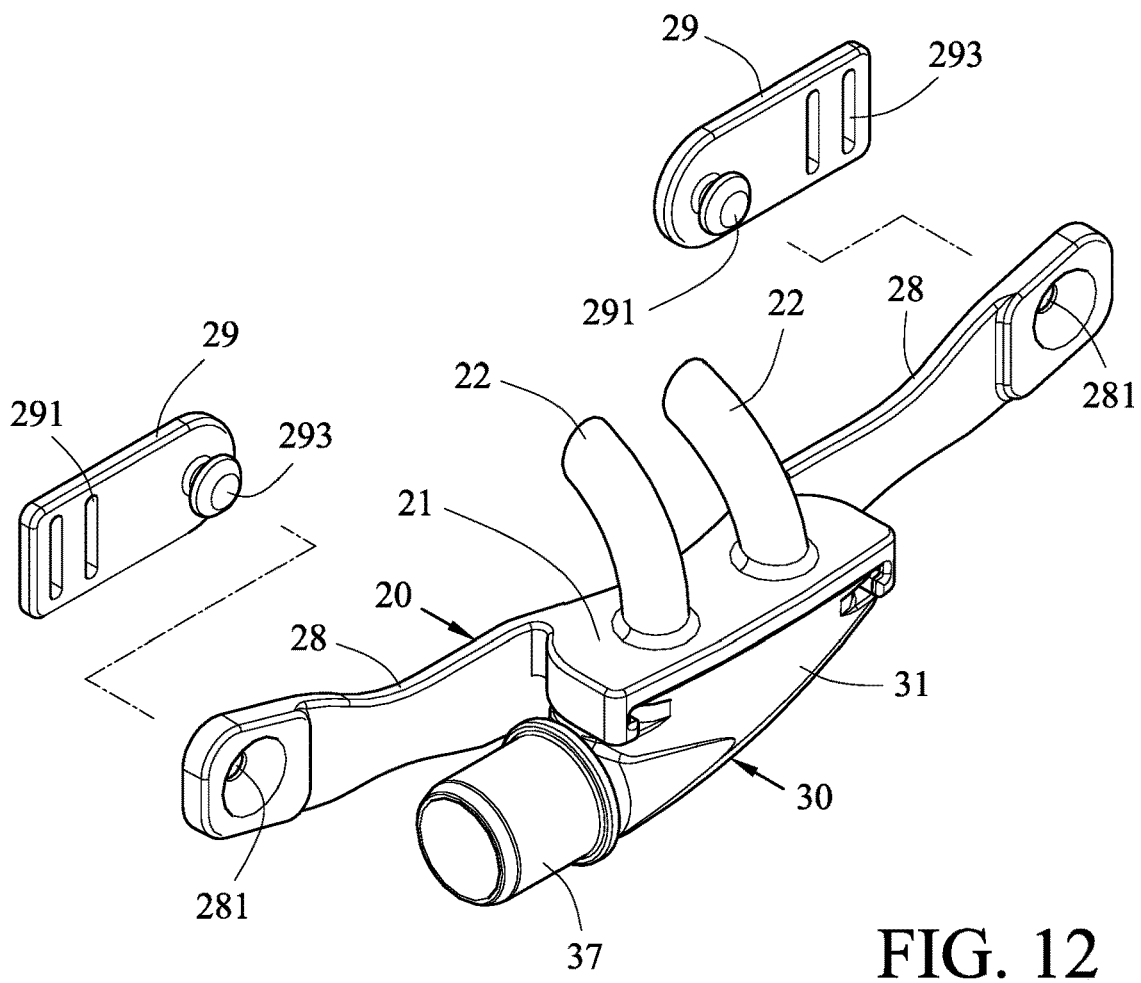
FIG. 12 is an exploded view showing the first preferred embodiment of the invention and a strap fastener.

Referring to FIG. 12, examples of the additional components of the intake tube 30 will be illustrated below, the nasal prong body 20 has a pair of extending wings 28, a pair of strap fasteners 29 can be respectively fixed on the extending wings 28 (for example, each of the extending wings 28 has a fixing hole 281, each of the strap fasteners 29 has a T-shaped post 291, each of the T-shaped posts 291 can be inserted into each of the fixing holes 281), each of the strap fasteners 29 has a plurality of strap holes 293 for wearing a strap (not shown).

Figure 13:
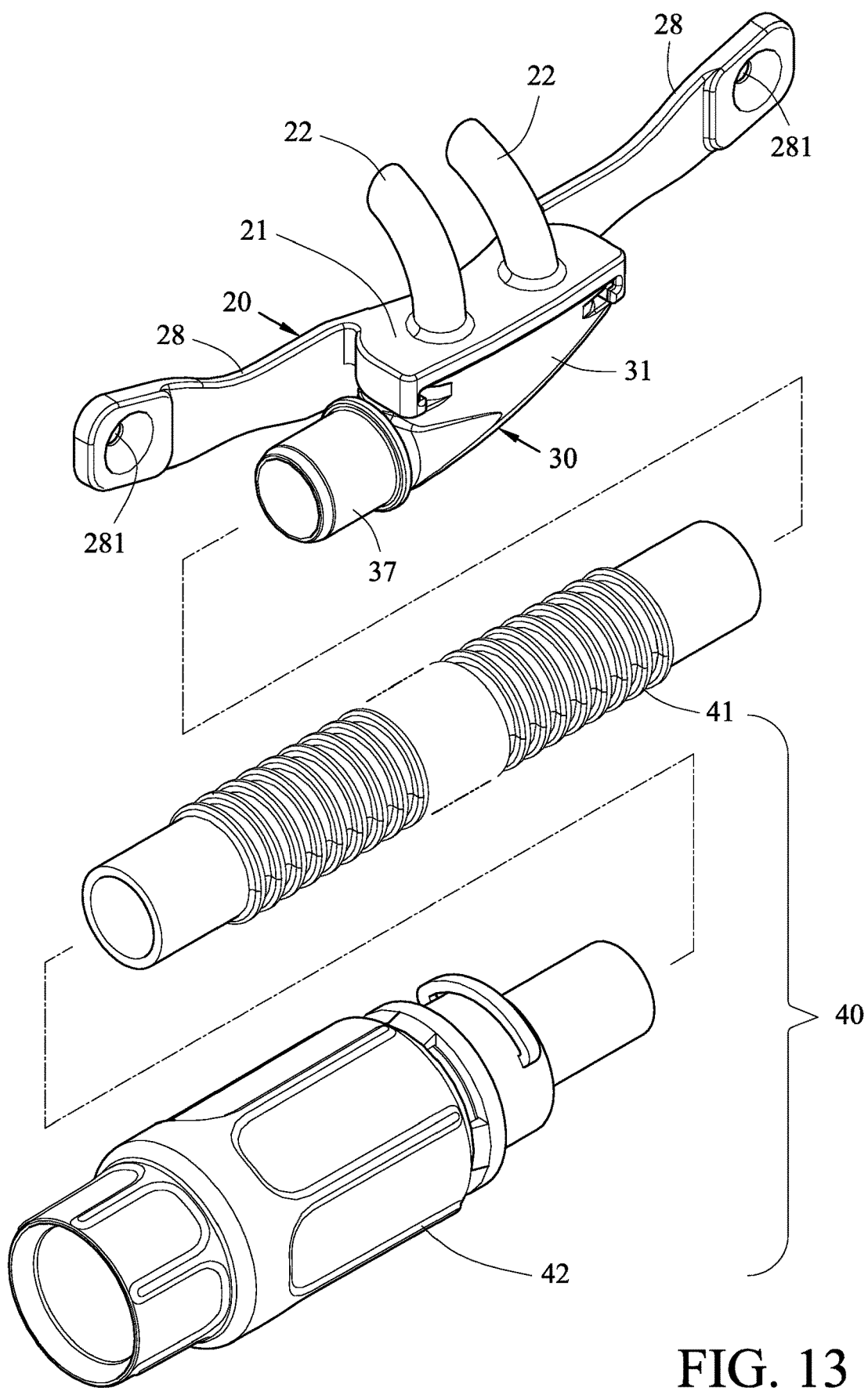
FIG. 13 is an exploded view showing the first preferred embodiment of the invention and a gas supply tube assembly.

Referring to FIG. 13, a gas supply tube assembly 40 can be further connected to the intake tube 30, examples of the gas supply tube assembly 40 will be illustrated below, a breathing tube 41 can be connected to the connecting portion 37 of the intake tube 30, the connecting portion 37 of the intake tube 30 can be located in a left direction L1 of the nasal prong body 20 or a right direction R1 of the nasal prong body 20; the extending direction of the breathing tube 41 can be located in the left direction L1 of the nasal prong body 20 (please also refer to FIGS. 1, 7 and 8) or the right direction R1 of the nasal prong body 20 (please also refer to FIGS. 2, 9 and 10); furthermore, a tubing connector 42 can be further connected to the breathing tube 41.

Examples of the function of the sliding track frame 10 will be illustrated below, two tracks 12 of the sliding track frame 10 can limit the moving direction of the first convex portions 32 of the flow guiding portion 31, therefore the first convex portions 32 of the flow guiding portion 31 can synchronously slide along the track direction S1 of the sliding track frame 10, the flow guiding portion 31 will be not easily offset. Moreover, the flow guiding portion 31 is not easily separated from the tracks 12 of the sliding track frame 10 when the breathing tube 41 is inadvertently pulled.

What is claimed is:

1. A nasal cannula having sliding track mechanism, the nasal cannula comprising:
    a rigid sliding track frame (10) of plastic material, two sides of the sliding track frame (10) respectively have a track (12) and a guide portion (16), a through hole (13) is formed on the sliding track frame (10);
    a flexible nasal prong body (20), the flexible nasal prong body (20) is combined with the sliding track frame (10) by means of injection molding, wherein the sliding track frame (10) is inserted into an elastic portion (21) of the flexible nasal prong body (20) whereby a pair of lateral walls (26) of the nasal prong body (20) are positioned adjacent to each of the guide portions (16), an outside of the elastic portion (21) is provided with a pair of nasal prongs (22), an inside of the elastic portion (21) is provided with a sealing surface (25), and the sealing surface (25) is located at the through hole (13) of the sliding track frame (10);
    a rigid intake tube (30) of plastic material, one side of the intake tube (30) has a flow guiding portion (31), and the flow guiding portion (31) has a pair of first convex portions (32) and a pair of guiding surfaces (36);
    wherein each of the first convex portions (32) can be inserted into each of the tracks (12), each of nasal prongs (22) can be fluid communicated to an opening (34) of the flow guiding portion (31), a flange (35) of the opening (34) can be pressed against the sealing surface (25),
    whereby the intake tube (30) abuts the pair of lateral walls (26) of the nasal prong body (20) and each of the guiding portions (16) of the sliding track frame (10) at the pair of guiding surfaces (36) of the intake tube (30), such that the first convex portions (32) of the intake tube (30) are slidably inserted perpendicular to a pair of extending wings (28) located on the nasal prong body (20), so that each of the tracks (12) of the sliding track frame and the flange (35) at the apex of the first convex portions (32) of the intake tube (30) such that the opening (34) of the intake tube (30) engages the sealing surface (25) of the nasal prong body (20).

2. The nasal cannula having sliding track mechanism of claim 1, wherein each of the first convex portions (32) can be formed a shape of curved surface, each of the first convex portions (32) can be easily inserted into each of the tracks (12) when the rigid sliding track frame (10) of plastic material is combined with the flow guiding portion (31) of the rigid intake tube (30) of plastic material.

3. The nasal cannula having sliding track mechanism of claim 1, wherein the material of the nasal prong body (20) can select from Silicone, Thermo-Plastic-Rubber (TPR), Thermoplastic Elastomer (TPE), Thermoplastic Urethane (TPU).

4. The nasal cannula having sliding track mechanism of claim 1, wherein the tracks (12) are symmetrically disposed on the rigid sliding track frame (10) of plastic material, the first convex portions (32) are symmetrically disposed on the flow guiding portion (31), therefore the combination direction of the rigid intake tube (30) of plastic material and the rigid sliding track frame (10) of plastic material can be quickly changed; thereby locating a connecting portion (37) of the rigid intake tube (30) of plastic material in a left direction (L1) of the flexible nasal prong body (20) or a right direction (R1) of the flexible nasal prong body (20).

5. The nasal cannula having sliding track mechanism of claim 1, wherein a pair of strap fasteners (29) can be respectively fixed on the extending wings (28), each of the strap fasteners (29) has a plurality of strap holes (293).

6. The nasal cannula having sliding track mechanism of claim 1, wherein a breathing tube (41) can be connected to a connecting portion (37) of the rigid intake tube (30) of plastic material, the connecting portion (37) of the rigid intake tube (30) of plastic material can be located in a left direction (L1) of the flexible nasal prong body (20) or a right direction (R1) of the flexible nasal prong body (20); thereby locating the extending direction of the breathing tube (41) in the left direction (L1) of the flexible nasal prong body (20) or the right direction (R1) of the flexible nasal prong body (20).

7. The nasal cannula having sliding track mechanism of claim 1, wherein a breathing tube (41) can be connected to a connecting portion (37) of the rigid intake tube (30) of plastic material, a tubing connector (42) can be further connected to the breathing tube (41).

8. The nasal cannula having sliding track mechanism of claim 1, wherein each of the guiding portions (16) can slide on each of the guiding surfaces (36) when the rigid sliding track frame (10) of plastic material is combined with the guiding portion (31) of the rigid intake tube (30) of plastic material, and thereby guiding each of the first convex portions (32) to insert into each of the tracks (12).

9. The nasal cannula having sliding track mechanism of claim 8, wherein the flexible nasal prong body (20) has a stopping portion (24), the stopping portion (24) can be pressed against a first rib portion (14) of the rigid sliding track frame (10) of plastic material, a second rib portion (15) of the rigid sliding track frame (10) of plastic material can be fixed to a groove (251) of the flexible nasal prong body (20), the groove (251) is adjacent to the elastic portion (21), the flexible nasal prong body (20) has a pair of lateral walls (26), each of the guiding portions (16) can be fixed between the lateral walls (26) and the elastic portion (21).

10. The nasal cannula having sliding track mechanism of claim 8, wherein the flow guiding portion (31) has a pair of upright wall surfaces (311), each of the upright wall surfaces (311) is located between each of the first convex portions (32) and each of the guiding surfaces (36).

* * * * *